United States Patent [19]

Ratton

[11] Patent Number: 4,851,566

[45] Date of Patent: Jul. 25, 1989

[54] PROCESS FOR PRODUCING ORGANIC COMPOUNDS CONTAINING AN ALKOXYALKYLIDENE GROUP

[75] Inventor: Serge Ratton, La Verpilliere, France

[73] Assignee: Rhone-Poulenc Specialites Chimiques, Courbevoie, France

[21] Appl. No.: 169,143

[22] Filed: Mar. 10, 1988

Related U.S. Application Data

[63] Continuation of Ser. No. 882,202, Jul. 3, 1986, abandoned, which is a continuation of Ser. No. 698,371, Feb. 1, 1985, abandoned.

[30] Foreign Application Priority Data

Feb. 7, 1984 [FR]  France ................ 84 02027

[51] Int. Cl.$^4$ .............................. C07C 69/73
[52] U.S. Cl. .................................... 560/181
[58] Field of Search ............ 560/181; 562/583; 502/170, 226, 340

[56] References Cited

U.S. PATENT DOCUMENTS

| 2,824,121 | 2/1958 | Nicholl et al. ........ | 560/181 |
| 3,118,949 | 1/1964 | Cull et al. ........... | 502/170 |
| 4,058,553 | 11/1977 | Ackermann et al. ..... | 560/180 |
| 4,503,074 | 3/1985 | Friedman et al. ...... | 560/181 |

FOREIGN PATENT DOCUMENTS

| 950883 | 6/1946 | France . |
| 2273793 | 1/1976 | France . |
| 41-4776 | 3/1966 | Japan . |

OTHER PUBLICATIONS

Claisen, *Ueber die Oxymethylenderivate des Acetessigathers, des Acetylacetons und des Malonsaureathers*, Ber 26, 2729 (1893).
Claisen, *Untersuchungen uber Oxymethylenverbindungen*, Annalen der Chemie 297, 16 (1897).
Sah *Condensation of Ortho Esters with Acetoacetic Ester and Malonic Ester*, J. Am. Chem. Soc. 53, 1836 (1931).
Post and Erickson, *The Reactions of Ortho Esters with Certain Acid Anhydrides*, J. Am. Soc. 2, 260 (1937).
Fuson, Parham and Reed, *Alkylation of Ethyl Malonate with Diethoxymethyl Acetate*, J. Org. Chem. 11, 194 (1946).

Primary Examiner—Bruce D. Gray
Attorney, Agent, or Firm—Finnegan, Henderson, Farabow, Garrett, & Dunner

[57] ABSTRACT

Process for preparing alkyl alkoxyalkylidenemalonate. An alkyl malonate is condensed with an orthoester in the presence of a carboxylic acid or its anhydride and a metal compound of the group formed by Cd, Hg, Bi, Mg.

23 Claims, No Drawings

PROCESS FOR PRODUCING ORGANIC COMPOUNDS CONTAINING AN ALKOXYALKYLIDENE GROUP

This application is a continuation of application Ser. No. 882,202, filed July 3, 1986, abandoned, which is a continuation of application Ser. No. 698,371 filed Feb. 1, 1985, abandoned.

The present invention has as its subject a process for producing compounds containing an alkoxylalkylidene group, and more especially a process for producing alkyl alkoxyalkylidenemalonates by condensation of an orthoester with an alkyl malonate.

The organic compounds which contain an alkoxyalkylidene group corresponding to the general formula:

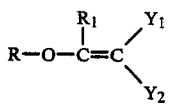

in which R denotes an alkyl radical, $R_1$ a hydrogen atom, alkyl radical or phenyl group, and $Y_1$ and $Y_2$, which may be identical or different, denote an alkyloxycarbonyl, nitrile or alkylcarbonyl residue, are intermediates which are in particular demand in organic synthesis. Thus alkyl alkoxymethylene malonates are used for producing alkyl anilinomethylenemalonates which are synthesis intermediates for substituted quinolines such as 4,7-dichloroquinoline or 4-chloro-7-(trifluoromethyl)quinoline (cf. French Pat. No. 950,883).

Alkyl alkoxyalkylidenemalonates are obtained by condensing an alkyl malonate (for example ethyl malonate) with an orthoester: alkyl, and especially methyl or ethyl, orthoformates, orthoacetates and orthobenzoates, cf. L CLAISEN, Ber. 26 page 2729 et seq. (1893) and Ann. 297 page 16 et seq. (1897); P. SAH, J. Am. Chem. Soc. 53 page 1836 et seq. (1931). This condensation, which can be represented by the following reaction scheme:

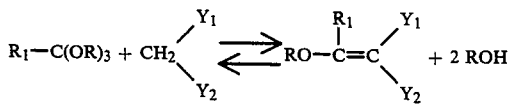

is generally performed in the presence of zinc chloride as catatylst and acetic anhydride as condensing agent. This reaction has formed the subject of several mechanistic studies [cf. H. W. Post et al., J. Org. Chem. 2 page 260 et seq. (1937) and R. C. FUSON et al., J. Org. Chem. 11 page 194 et seq. (1946)], especially with the object of improving the yields of alkoxymethylenemalonates (cf. R. C. FUSON et al., loc. cit.). Thereafter, several improvements to the CLAISEN process where proposed with the object of raising the yields of alkyl alkoxymethylenemalonates (especially with respect to the orthoformates) and the productivity of the reaction. In U.S. Pat. No. 2,824,121, it was proposed that the condensation should be carried out in the absence of zinc chloride, that the acetic anhydride should be replaced by an amount of acetic acid insufficient to block, in the form of acetate, the alcohol formed during the reaction, and that this alcohol should be removed by distillation as it formed. Despite the improvement in results obtained thereby, this process did not lead to sufficient yields with respect to orthoformate. In the Japanese Patent Application published under No. 4776/66, it was recommended to work in the presence of metal catalyst (zinc salts and iron salts) in the absence of acid or anhydride, in a hydrocarbon solvent (benzene, xylene, toluene), providing for removal of the alcohol formed by azeotropic distillation. The yields ascribed to this process could not be confirmed. Finally, in French Patent Application No. 75/17,177, published under No. 2,273,793, it has been proposed that alkyl alkoxymethylenemalonates should be prepared by reacting an alkyl malonate with an excess of alkyl orthoformate at 100°-160° C. in the presence of a zinc, aluminum or iron salt, removing the alcohol resulting from the condensation as it formed. In spite of the improvement in yields which it brings about, this process does not enable a theoretical yield of alkoxymethylenemalonate of 90%, relative to the orthoformate, to be exceeded, so that industry is still in search of means for increasing this yield. Orthoformates constitute, in fact, an expensive raw material, and any improvement in their conversion to alkoxymethylenemalonates involves a substantial reduction in their prime cost.

One of the subjects of the present invention lies precisely in the improvement in yields of alkoxylalkylenemalonates with respect to orthoesters and, incidentally, with respect to malonates. Another subject of the present invention lies in an enlargement in the choice of condensation catalysts.

More specifically, the present invention has as its subject a process for preparing alkyl alkoxylalkylidenemalonates by condensing an alkyl malonate with an orthoester in the presence of a carboxylic acid or its anhydride and a metal derivative as catalyst, wherein the latter is chosen from the group formed by cadmium compounds, magnesium compounds, bismuth compounds and mercury compounds.

Since the publications of L. CLAISEN, loc. cit., zinc chloride is the catalyst most commonly used because it leads to the best results. In Japanese Patent Application No. 4776/66 and in French Patent Application No. 75/17,177, the use of aluminum chloride and ferric chloride were well described, but these compounds possess lower efficiency than that of zinc chloride; the yields of alkoxymethylenemalonates they bring about, are, in fact, greatly inferior to those obtained with zinc chloride. Although the abovementioned French Application refers to the general use of Lewis acids for catalysis of the condensation of malonates with orthoformates, the choice of compounds of Cd, Hg, Bi and Mg could not be suggested by the prior art. It is known, in fact, that Lewis acids form a vast group of metal compounds, the catalytic activity of which is extremely variable from one metal to another (cf. G. A. OLAH, Friedel-Crafts and Related Reactions, Vol. 1, pages 33 to 34 and pages 169 to 291). It hence appears unexpected that, among a group of Lewis acids comprising inactive metals or metals less active than zinc chloride for preparing alkyl alkoxymethylenemalonates, compounds of Cd, Hg, Bi and Mg lead to results better than or practically equivalent to those of zinc chloride.

Any inorganic or organic acid salt of Cd, Hg, Bi and Mg can be used, such as halides, sulfates, nitrates, carbonates, phosphates, carboxylates and sulfonates. For practical reasons, use is preferably made of halides (more especially chlorides and bromides) and carboxylates. In the latter case, it is possible to use the Cd, Hg, Bi and Mg salts of any carboxylic acid, such as saturated or unsaturated aliphatic or cycloaliphatic, or aromatic, mono- or polycarboxylic acids. There may be mentioned especially the salts of formic, acetic, propionic, butyric, pentanoic, hexanoic, octanoic, dodecanoic, hexadecanoic, stearic and oleic acids, or of mixtures of fatty acids such as naphthenic acid, the acid sold under the trade name "Versatic Acid" and benzoic acid. In practice, use is preferably made of chlorides and bromides of Cd, Hg, Bi and Mg, and carboxylates of lower aliphatic acids. Without implied limitation, there may be mentioned cadmium chloride, cadmium bromide, magnesium chloride and bromide, mercuric chloride and bromide, bismuth chloride ($BiCl_3$) and bismuth ($BiBr_3$), cadmium acetate [$Cd(C_2H_3O_2)_2$], cadmium benzoate, cadmium oxalate, cadmium salicylate, bismuth acetate [$Bi(C_2H_3O_2)_3$], bismuth benzoate, mercuric acetate [$Hg(C_2H_3O_2)_2$], mercuric benzoate, mercuric oxalate, magnesium acetate, magnesium benzoate, magnesium laurate, magnesium oxalate, magnesium palmitate and magnesium stearate. In practice, there are preferably chosen the Cd, Hg, Bi and Mg carboxylates which correspond to the acid or acid anhydride used as condensing agent. It is immaterial whether these salts are used in anhydrous or hydrated form. It is also possible to mix two or more than two of these derivatives, or mix on of them with the compounds previously used as catalysts ($ZnCl_2$, $AlCl_3$ and $FeCl_3$).

The amount of metal compound expressed in gram-ion of metal per mole of alkyl malonate can vary between wide limits. In practice, this amount can vary between limits ranging from $1 \times 10^{-5}$ to $1 \times 10^{-2}$ gram-ion of metal per mole of alkyl malonate, and preferably from $1 \times 10^{-4}$ to $1 \times 10^{-3}$ gram-ion per mole.

By way of condensing agent, aliphatic carboxylic acids and their anhydride, and more especially lower aliphatic acids containing 1 to 5 carbon atoms and their anhydride, are preferably used. There may be mentioned, in particular, formic acid, acetic acid, propionic acid and pivalic acid.

The catalysts according to the present invention can be used under the general conditions for condensation indicated in the prior art mentioned above. Thus, the reaction temperature can be between 80° and 180° C., and preferably between 100° and 170° C.; it is possible to use the stoichiometric amount of orthoester or an excess of orthoester relative to the alkyl malonate, so that the amount of orthoester can vary between 1 mole and 5 moles per mole of malonate, preferably between 1.2 and 4 moles per mole. The amount of carboxylic acid or anhydride can be less than or equal to 1 mole per mole of malonate; it is preferable to use an amount of carboxylic acid or anhydride ranging from 0.01 mole to 0.3 mole per mole of malonate. In this case, the alcohol generated during the condensation is preferably removed as it forms, for example by distillation according to the teaching of U.S. Pat. No. 2,824,121.

The process according to the invention is especially well suited to the preparation of alkyl alkoxyalkylidenemalonates of formula:

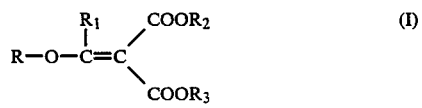

(I)

in which:

R denotes an alkyl radical containing 1 to 4 carbon atoms, and preferably a methyl or ethyl radical;

$R_1$ denotes a hydrogen atom or a methyl, ethyl or phenyl radical; .

$R_2$ and $R_3$, which may be identical or different, denote alkyl radicals containing 1 to 4 carbon atoms, and may be identical or different from R and are preferably methyl or ethyl radicals.

The process is preferably used for preparing alkyl alkoxymethylenemalonates and especially methyl or ethyl methoxy- or ethoxymethylenemalonates by reacting methyl or ethyl malonate with methyl or ethyl orthoformate.

From a practical standpoint, the total quantity of the reactants, the catalyst and the carboxylic acid or its anhydride can be brought into contact from the beginning of the reaction or, accordance to a variant of procedure, it is possible to charge a reaction apparatus with the total quantity of the malonate and catalyst and a part of the orthoester and the carboxylic acid or its anhydride, bring this charge to a suitable temperature and then add, continuously or portionwise, the remainder of the orthoester and the carboxylic acid or its anhydride as the reaction progresses, the progress being monitored on the basis of the amount of alcohol removed. The reaction time depends on the working conditions used. Under certain conditions, after the malonate has disappeared, it can be advantageous to maintain the reacting mass at the reaction temperature for a period needed for conversion of the reaction intermediates, especially dialkoxymethylene malonates, to alkoxymethylenemalonates. Thus, the heating may be continued until the alcohol generated by the reaction ceases to be distilled. When the condensation is complete, the reacting mass is treated to separate its different constituents: excess orthoester, alkoxyalkylidenemalonate, acid or acid anhydride and/or their esters, byproducts of the reaction and metal compound. The organic compounds are preferably separated by distillation. It is advantageous to separate the metal catalyst from the reacting mass before distilling the latter, since it has been observed that metal derivatives encourage thermal decomposition of alkoxyalkylidenemalonates during this procedure. In this connection, the use of a cadmium salt proves especially advantageous by virtue of its ease of separation from the reacting mass: it is sufficient, at the end of the reaction, to lower the temperature of the mixture obtained to cause the separation of the metal compound at the bottom of the reaction vessel, and the upper organic layer is then drawn off and the catalytic residue left in the reaction apparatus for a further process. With the catalysts of the prior art (zinc chloride, aluminum chloride, ferric chloride), it was necessary to resort to removing the metal compound by extraction with water, which process proves more complicated and costly.

The examples which follow illustrate the invention and show how it can be put into practice.

EXAMPLE 1

In a 1-liter glass three-necked flask equipped with a thermometer, central stirrer, distillation column, column head, condenser, separator, receiver and electric heating device, there are charged:

| | |
|---|---|
| diethyl malonate | 163.8 g (1.024 mole) |
| ethyl orthoformate | 444 g (3 moles) |
| anhydrous acetic acid | 3 g (0.05 mole) |

| | |
|---|---|
| Cd (CH$_3$COO)$_2$. 2 H$_2$O | 0.134 g (5 × 10$^{-4}$ mole) | and the contents of the flask are heated gradually to the refluxing temperature. The temperature of the vapor is adjusted to approximately 78°-79° C., and the volatile reaction products (ethanol in particular) are drawn off. Distillation begins after 30 minutes' heating at 148°-151° C.

The temperature of the reacting mass rises gradually from 148° to 157° C. at the end of the reaction. After 5 h 30 min of reaction, the diethyl malonate (DEM) is determined by gas chromatography on an aliquot portion of the reacting mass. It is observed that their remains 0.1 g of DEM. 92.8 g of distillate have been collected in total. The reacting mass is maintained for a further 2 hours at 157° C. A supplementary amount of distillate of 9.34 g is collected. In total, 102.14 g of a distillate have been isolated which consists mainly of ethanol containing methyl acetate and formate.

The reacting mass is cooled to 20° C., and the unconverted diethylmalonate (DEM), the ethyl orthoformate (EOF) and the ethyl ethoxymethylenemalonate (EEMM) formed are determined by gas chromatography. The results obtained are as follows:
DEM: 0.1 g, or a degree of conversion of 100%
EOF: 284.7 g, or a degree of conversion of 35.8%
EEMM: 219.3 g.

The yields of EEMM relative to the DEM and EOF converted (CY) amount respectively to 99.2% and 94.3%.

EXAMPLE 2

Example 1 was repeated, using 0.067 g (2.5×10$^{-4}$ mole) of the cadmium acetate. Under these conditions, CY values were obtained relative to DEM and EOF which amounted respectively to 98.8% and 94.4%.

EXAMPLES 3 to 5

Example 1 was repeated, replacing cadmium acetate by mercuric acetate (2.5×10$^{-4}$ mole), magnesium chloride hexahydrate (1×10$^{-3}$ mole) and bismuth chloride (3×10$^{-4}$).

The following results were obtained:

| Examples | DC DEM | DC EOF | EEMM determined in g | CY DEM % | EEMM EOF % |
|---|---|---|---|---|---|
| 3 | 100% | 36.2% | 192.3 | 87 | 82 |
| 4 | 100% | 34.9% | 210.9 | 95.3 | 93.2 |
| 5 | 100% | 34.61% | 198.6 | 90 | 88.5 |

EXAMPLE 6

In the apparatus described in Example 1 to which a dropping funnel has been added, there are charged:

| | |
|---|---|
| EOF | 334 g |
| DEM | 163.8 g |
| acetic acid | 3 g |
| MgCl$_2$. 6 H$_2$O | 0.218 g | and the temperature of the flask is brought to 151° C. in the course of 25 minutes. Reaction starts and the ethanol formed begins to distill. Ethyl orthoformate is then added continuously in an amount equivalent to the volume of the distillate. The temperature of the reacting mass is maintained at 155/156° C. After 3 h 30 min under these conditions, 126 ml of distillate has been collected and 126 ml (110 g) of EOF has been added. A determination carried out on an aliquot portion of the reacting mass shows that all the DEM has been converted. The reacting mass is maintained for 2 hours at 156/157° C., during which time a supplementary amount of distillate of 10 ml is collected.

The reacting mass is cooled to 20° C. and weighed; its weight amounts to 501.49 g. On an aliquot portion, the EOF and the products formed are determined by gas chromatography. It is observed that there remain 280.5 g of EOF and that 211.3 g of EEMM have been formed.

The yields of EEMM relative to the DEM and EOF converted are respectively 95.55% and 88.5%.

I claim:

1. A process for preparing an alkyl alkoxyalkylidenemalonate comprising the step of condensing an alkyl malonate with a suitable orthoester in the presence of (1) a condensing agent comprising a suitable carboxylic acid or the anhydride of a carboxylic acid, and (2) a catalytically effective amount of a metal catalyst for the condensation reaction, said catalyst being selected from the group consisting of a cadmium compounds and magnesium compounds.

2. The process of claim 1, wherein said alkoxyalkylidenemalonate prepared is of the formula:

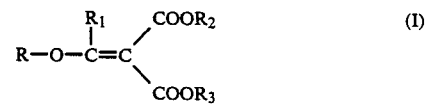

in which
R denotes an alkyl radical containing 1 to 4 carbon atoms;
R$_1$ denotes a hydrogen atom, or a methyl, ethyl or phenyl radical;
R$_2$ and R$_3$, which may be identical or different, denote alkyl radicals containing 1 to 4 carbon atoms, and R$_2$ and R$_3$ may each be identical to or different from R.

3. The process of claim 1, wherein diethyl ethoxymethylenemalonate is prepared by reacting diethyl malonate with ethyl orthoformate.

4. The process of claim 1, wherein dimethyl methoxymethylenemalonate is prepared by reacting dimethyl malonate with methyl orthoformate.

5. The process of claim 1, wherein said metal catalyst is a salt of an inorganic or carboxylic acid.

6. The process of claim 1, wherein said metal catalyst is selected from the group consisting of a cadmium carboxylate, cadmium chloride, cadmium bromide, a magnesium carboxylate, magnesium chloride and magnesium bromide.

7. The process of claim 6, wherein said magnesium chloride is magnesium chloride hexahydrate and wherein said cadmium carboxylate is cadmium acetate.

8. The process of claim 1, wherein the amount of metal catalyst expressed in gram-ion of metal per mole of malonate is from about 1×10$^{-5}$ to about 1×10$^{-2}$ gram-ion per mole.

9. The process of claim 8, wherein the amount of metal catalyst is from about 1×10$^{-4}$ to about 1×10$^{-3}$ gram-ion per mole.

10. The process of claim 9, wherein the amount of metal catalyst is from about $2.5\times10^{-4}$ to about $1\times10^{-3}$ gram-ion per mole.

11. The process of claim 1, wherein the amount of carboxylic acid or anhydride is from about 0.01 to about 1 mole per mole of malonate.

12. The process of claim 11, wherein the amount of carboxylic acid or anhydride is from about 0.01 to about 0.3 mole per mole of malonate.

13. The process of claim 12, wherein the amount of carboxylic acid or anhydride is about 0.05 mole per mole of malonate.

14. The process of claim 1, wherein the amount of orthoester is from about 1 to about 5 moles per mole of malonate.

15. The process of claim 14, wherein the amount of orthoester is from about 1.2 to 4 moles per mole of malonate.

16. The process of claim 15, wherein the amount of orthoester is about 3 moles per mole of malonate.

17. The process of claim 1, wherein the reaction temperature is from about 80° to 180° C.

18. The process of claim 17, wherein the reaction temperature is from about 100° to 170° C.

19. The process of claim 18, wherein the reaction temperature is from about 148° to about 157° C.

20. The process of claim 1, wherein said alkoxyalkylidenemalonate prepared is of the formula

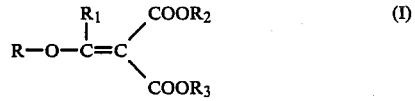

in which
R denotes an alkyl radical containing 1 to 4 carbon atoms;
$R_1$ denotes a hydrogen atom, or a methyl, ethyl or phenyl radical;
$R_2$ and $R_3$, which may be identical or different, denote alkyl radicals containing 1 to 4 carbon atoms, and $R_2$ and $R_3$ may each be identical to or different from R;
wherein said metal catalyst is selected from the group consisting of cadium acetate and magnesium chloride,
wherein the amount of metal catalyst expressed in gram-ion of metal per mole of malonate is from about $2.5\times10^{-4}$ to about $1\times10^{-3}$ gram-ion per mole,
wherein the amount of carboxylic acid or anhydride is about 0.05 mole per mole of malonate,
wherein the amount of orthoester is about 3 moles per mole of malonate and;
wherein the reaction temperature is from about 148° to about 157° C.

21. The process of claim 2, wherein said metal catalyst is selected from the group consisting of a cadmium carboxylate, cadmium chloride, cadmium bromate, a magnesium carboxylate, magnesium chloride and magnesium bromide.

22. The process of claim 1, wherein said metal catalyst is a cadmium compound.

23. The process of claim 22, wherein said metal catalyst is cadmium acetate.

* * * * *

UNITED STATES PATENT AND TRADEMARK OFFICE
CERTIFICATE OF CORRECTION

PATENT NO.   : 4,851,566

DATED        : July 25, 1989

INVENTOR(S)  : Serge Ratton

It is certified that error appears in the above-identified patent and that said Letters Patent is hereby corrected as shown below:

Claim 1, column 6, line 25, change "of a" to --of--.

Signed and Sealed this

Twenty-eighth Day of August, 1990

Attest:

HARRY F. MANBECK, JR.

Attesting Officer

Commissioner of Patents and Trademarks